United States Patent
Place

Patent Number: 5,855,548
Date of Patent: Jan. 5, 1999

[54] VENOUS FLOW CONTROL ELEMENT FOR MAINTAINING PENILE ERECTION

[75] Inventor: Virgil A. Place, Kawaihae, Hi.

[73] Assignee: Vivus, Incorporated, Mountain View, Calif.

[21] Appl. No.: 782,867

[22] Filed: Jan. 10, 1997

Related U.S. Application Data

[63] Continuation-in-part of Ser. No. 664,423, Jun. 14, 1996, abandoned.

[51] Int. Cl.⁶ .................................................. A61F 5/00
[52] U.S. Cl. ............................... 600/38; 600/41; 128/885
[58] Field of Search .............................. 600/29, 30, 38, 600/39, 41; 604/48, 49, 51; 128/885, DIG. 25

[56] References Cited

U.S. PATENT DOCUMENTS

| | | |
|---|---|---|
| 515,367 | 2/1894 | Rounseville . |
| 678,943 | 7/1901 | Davis .................................... 128/885 |
| 2,581,114 | 1/1952 | Larson . |
| 3,461,863 | 8/1969 | Sullinger . |
| 3,910,280 | 10/1975 | Talonn . |
| 4,069,825 | 1/1978 | Akiyama . |
| 4,127,118 | 11/1978 | Latorre . |
| 4,203,432 | 5/1980 | Koch . |
| 4,760,846 | 8/1988 | Mers Kelly et al. . |
| 4,801,587 | 1/1989 | Voss et al. . |
| 4,857,059 | 8/1989 | Rey et al. . |
| 4,911,162 | 3/1990 | Wolff . |
| 4,967,738 | 11/1990 | March . |
| 5,027,800 | 7/1991 | Rowland . |
| 5,085,209 | 2/1992 | Gottschalk . |
| 5,123,913 | 6/1992 | Wilk et al. . |
| 5,207,694 | 5/1993 | Broome . |
| 5,242,391 | 9/1993 | Place et al. . |
| 5,342,834 | 8/1994 | Bardin et al. ......................... 514/178 |
| 5,350,399 | 9/1994 | Erlebacher et al. . |
| 5,387,179 | 2/1995 | Crivellaro . |

FOREIGN PATENT DOCUMENTS

| | | |
|---|---|---|
| 0 266 968 | 5/1998 | European Pat. Off. . |
| WO 90/11063 | 10/1990 | WIPO . |
| WO91/16021 | 10/1991 | WIPO . |

OTHER PUBLICATIONS

Sidi et al., "Simplified Tourniquet for Intracavernous Pharmacotherapy," *Urologic Clinics of North America*, 17(1):19–21 (1990).

*Primary Examiner*—Jennifer Bahr
*Assistant Examiner*—Rosiland Kearney
*Attorney, Agent, or Firm*—Dianne E. Reed; Bozicevic & Reed LLP

[57] ABSTRACT

A venous flow control device is provided for assisting in the maintenance of a penile erection or in preventing urinary incontinence. The device is a tubular structure adapted to be secured in a loop configuration about the penis to provide an adjustable radial constrictive force about the base of the penis. Methods for using the device are also provided.

32 Claims, 3 Drawing Sheets

VENOUS FLOW CONTROL ELEMENT FOR MAINTAINING PENILE ERECTION

CROSS-REFERENCE TO RELATED APPLICATION

This application is a continuation-in-part of U.S. patent application Ser. No. 08/664,423, filed Jun. 14, 1996 now abandoned.

TECHNICAL FIELD

The present invention relates generally to venous flow control devices useful for maintaining erection of the penis during sexual intercourse. More particularly, the invention pertains to a tubular device adapted to be secured in a loop configuration about an individual's penis in either a pre-scrotal or post-scrotal position. The invention additionally relates to methods of using the device to control venous flow from the penis, and to use in conjunction with the administration of pharmacologically active agents.

BACKGROUND OF THE INVENTION

Generally, an erection is produced by a blood flow imbalance caused by increased arterial blood flow into the erectile tissues of the penis in the presence of restricted veinal blood flow from the penis. This imbalance enables the erectile tissue to become engorged with blood and causes penile enlargement or erection. The physiological events associated with the erectile process include a vascularization which increases arterial blood flow into the penis as well as a concurrent veno-constriction from the expanding cavernosa compression against the tunica, thereby causing an imbalance in blood flow rates to and from the penis. Erection persists as long as arterial inflow exceeds venous outflow.

The erectile process can fail for a number of reasons, resulting in any one of a number of erectile dysfunctions, including impotence. "Impotence" is the consistent inability to achieve or sustain an erection of sufficient rigidity for sexual intercourse. It has been estimated that approximately 10 million American men are impotent (R. Shabsigh et al., "Evaluation of Erectile Impotence," *Urology* 32:83–90 (1988); W. L. Furlow, "Prevalence of Impotence in the United States," *Med. Aspects Hum. Sex.* 19:13–16 (1985)). Impotence is recognized to be an age-dependent disorder, with an incidence of 1.9 percent at 40 years of age and 25 percent at 65 years of age (A. C. Kinsey et al., "Age and Sexual Outlet," in *Sexual Behavior in the Human Male*, A. C. Kinsey et al., eds., Philadelphia, Pa.: W. B. Saunders, 218–262 (1948)). In 1985 in the United States, impotence accounted for more than several hundred thousand outpatient visits to physicians (National Center for Health Statistics, National Hospital Discharge Survey, 1985, Bethesda, Md., Department of Health and Human Services, 1989 DHHS publication no. 87-1751).

A number of causes of impotence have been identified, including vasculogenic, neurogenic, endocrinologic and psychogenic. See Das, S., *Int. J. Impotence Res.* 6:183–189 (1984). Impotence may result from various physiological or psychological conditions which cause the blood flow rates to and from the penis to remain substantially in balance, thereby preventing the concomitant retention of blood in the penis, which is necessary to induce and maintain an erection. Impotence can also be a side effect of various classes of therapeutic drugs, or can be associated with various diseases, including diabetes, multiple sclerosis and sickle cell anemia. Impotence resulting from any one of these causes can be exacerbated by additional factors such as cigarette smoking, a poor diet, or the like.

A frequent physiological condition associated with impotence relates to "venous leakage" wherein the penile venous system is not sufficiently compressed during the erectile process, permitting excessive drainage of blood from penile tissue and subsequent detumescence or erectile failure. Diagnostic tests (e.g., cavernosography) have shown that upwards of 40% of impotent men suffer from some degree of venous leakage.

Numerous treatments for impotence are known in the art, and include psychological therapies, hormonal therapy, administration of various vasodilators, surgery (e.g., vascular surgery or implantation of penile prostheses), vacuum devices and various external aids such as penile splints and constriction devices. See e.g., Krane, et al., *N. Eng. J. Med.* 321(24):1648–1659 (1989). In light of the recognition that penile inflow arteries are principally within the deep interior of the organ, and that penile return veins are disposed both within the deep interior and subdermally, adjacent to the surface of the organ, a number of devices have been described wherein the blood flow from the penis may be restricted using external devices such as constriction bands. These devices are adapted to be placed about the penis at a location closely adjacent to the body trunk. Thus, the blood flow from the penis via the peripheral veins is impeded while the blood flow to the penis via the deeply embedded arteries remains substantially unimpeded, thereby assisting in the achievement and/or maintenance of an erection (Sidi et al., *Urol. Clin. N. America*, 17:19–21 (1990); U.S. Pat. Nos. 2,581,114 to Larson; 3,461,863 to Sullinger; 4,203,432 to Koch; 4,967,738 to March; 5,027,800 to Rowland).

More particularly, U.S. Pat. No. 2,581,114 to Larson describes a constriction device consisting of an elongated elastic tube with a rigid U-shaped yoke which provides the "socket" of a ball-and-socket coupling means for fastening the device in place about a penis, and impeding venous outflow. U.S. Pat. No. 3,461,863 to Sullinger describes an adjustable constriction device consisting of a loop of flexible tubing having two apertures arranged at one end of the tubing which allow the other end to pass through and provide a means for fastening the device in place. Sullinger further describes the importance of the relative spacing of the two apertures and tube wall thickness to prevent or resist slippage of the device in response to increased tension. Sidi et al. describe a multi-component tourniquet device comprised of flexible tubing, an associated elongate locking mechanism, and a separate release loop. The flexible tubing is routed through a first aperture in the locking mechanism, doubled back to form a loop, and routed through a second aperture in the locking mechanism. The device is described for use in conjunction with the intracavernosal administration of drugs in the diagnosis and treatment of impotence.

Although these devices, as well as other types of constriction or clamping devices known in the art, are capable of restricting blood flow from the penis, these devices are subject to several disadvantages in the treatment or prevention of erectile failure. One common disadvantage involves a lack of a means to adjust constrictive tension, rendering it difficult or impossible to control the degree of veinal outflow restriction necessary to prevent erectile failure. Insufficient restriction may prevent such devices from maintaining an erection, and too much restriction may result in user discomfort, numbness and insensitivity, and may even result in damage to the penile tissue if left in place for an extended period of time. Prior devices which may exert excessive constriction can cause substantial or complete restriction of arterial blood flow into the penis, resulting in serious injury. Further, since the degree of veinal restriction provided by prior devices depends in part on the stage of the individual's erection, a problem arises when such devices are adjusted to a particular tightness suitable for achieving an initial erection that subsequently becomes too restrictive thereafter.

Other approaches to inducing erection and preventing erectile failure include physiological treatments such as injection of a vasoactive drug directly into a corpora cavernosa. See, for example, U.S. Pat. Nos. 4,127,118 to Latorre, 4,766,889 to Trick et al., and 4,857,059 to Rey et al. Commonly used drugs include α-adrenergic blocking agents such as the long acting phenoxybenzamine and the short acting phentolamine, smooth muscle relaxants such as papaverine, prostaglandins having vasoactive function such as prostaglandin-$E_1$ ($PGE_1$) and combinations thereof. See Kursh et al., *Urol. Clin. of No. America* 15(4):625–629 (1988), and Ishii et al., *J. of Urol.* 141:323–325 (1989). Yet another approach involves topical application of an agent such as a vasodilator directly to the various skins or mucosa of the penis. Commonly used agents include hydralazine, sodium nitroprusside, phenoxybenzamine and phentolamine (see U.S. Pat. No. 4,801,587 to Voss et al.). Although such therapies provide sufficient prevention of erectile failure in some individuals, loss of erection upon lying down or incomplete response to the vasoactive drugs at high dosages may be manifestations of excessive venous outflow from the penis. In such instances, the concurrent use of a venous outflow control device may be indicated.

Accordingly, there remains a need for a therapeutic device adapted for application to the penis that is useful to treat or prevent erectile failure. Such a device must be capable of providing readily adjustable control over venous outflow, whereby proper use thereof enhances retention of blood within an individual's penis without substantially obstructing arterial inflow or becoming too constrictive during the erectile process. Further, there remains a need for a venous flow control device which may be employed to supplement or improve the efficacy of physiological treatments for erectile failure, such as in the therapeutic administration of vasoactive or androgenic agents and the like. The devices may be used to reduce the required dosage, and/or to render effective a dosage which is ineffective in the absence of the device. That is, the administered agent remains within the penis for an extended period of time, and enhances the effectiveness of the drug therapy. It is also desirable that any such device be simple in structure, so as to provide ease and economy of manufacture.

SUMMARY OF THE INVENTION

Accordingly, it is a primary object of the invention to provide a novel device for the treatment or prevention of erectile dysfunction, wherein the device is formed from a length of flexible tubing capable of providing readily adjustable venous flow control when applied to the penis. The therapeutic device can thus be used to effectively enhance retention of blood within the penis without substantially obstructing arterial inflow or becoming too constrictive during the erectile process.

It is another object of the invention to provide a method of maintaining penile erection in a male individual by encircling the penis with an adjustable venous flow control device and securing the device at a selected tension to assist in preventing excess venous outflow from the individual's erect penis. The method can also be used to enhance penile erection, for example by enhancing penile size achieved with erection.

It is still a further object of the invention to provide a method of treating erectile dysfunction in a male individual by encircling the individual's penis with a venous flow control device and selecting a desired tension setting, then administering a pharmacologically active agent to the individual, whereby the device prevents excess venous outflow from the penis and causes enhanced retention of the agent within the penis. When used in conjunction with pharmaceutical therapy, for example, transurethral drug administration, the device helps retain the drug within the penis to allow transfer to the corpus cavernosum for an extended period of time. Use of the therapeutic device in this manner may render effective an otherwise ineffective dose of a pharmacologically active agent, and/or may reduce the dosage of the agent necessary to provide a therapeutic effect.

It is yet a further object of the invention to provide a method for preventing urinary incontinence in a male individual by encircling the penis with a venous flow control device as provided herein, and tensioning the device about the penis to prevent involuntary passage of urine from the urethra.

Additional objects, advantages and novel features of the invention will be set forth in part in the description which follows, and in part will become apparent to those skilled in the art in light of an examination of the following, or may be learned by practice of the invention.

DETAILED DESCRIPTION OF THE INVENTION

Before describing the present invention in detail, it is to be understood that the present invention is not limited to specific materials, configurations or particular methods of use, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "a vasoactive agent" refers to one or more such agents, reference to "an androgenic agent" includes a mixture of two or more such agents, and the like.

In describing and claiming the present invention, the following terminology will be used in accordance with the definitions set out below.

The term "elasticity" as used herein refers to the capability of a solid material to change shape and size under the influence of opposing forces, to sustain such deformation without permanent loss of size or shape, and to recover its original configuration when the forces are removed. Further, an "elastomer" or "an elastomeric material" generally refers to any substance which exhibits elasticity.

The elasticity of a material selected for use herein will derive from a number of factors such as "tensile strength" and tube wall thicknesses. "Tensile strength" refers to the maximum stress which a stretched material can withstand without tearing. The elasticity of a material may be qualified and quantified in a variety of ways. The elastic materials used to make the present devices are flexible and capable of regaining their original shape after being deformed within their elastic limits.

The term "erectile dysfunction" as used herein intends a periodic or consistent inability to achieve or sustain an erection of sufficient rigidity for sexual intercourse. The present method of "treating" erectile dysfunction includes "preventing" erectile dysfunction as well.

As used herein, the terms "drug" or "pharmacologically active agent" intend a compound or composition of matter which, when administered to an organism (human or animal) induces a desired therapeutic effect. Preferred pharmacologically active agents used in conjunction with the invention are vasoactive and androgenic agents.

The terms "transurethral," "intraurethral" or "urethral" as used to specify the preferred mode of administration of pharmacologically active agents, refer to delivery of at least one such agent into the urethra such that the agent contacts the lining thereof and passes therethrough into the vascular system of the spongiosa, glans and the corpora cavernosa of the penis.

The term "topical" is used herein to refer to a mode of administration of various agents at, or immediately beneath, the point of application to the skin or mucosa. A large number of chemical agents can be applied to the various skins or urethral mucosa of the penis for their local and sometimes systemic effects.

By "transdermal" delivery, applicants intend to include both transdermal (or "percutaneous") and transmucosal administration, i.e., delivery by passage of a drug through the skin or mucosal tissue and into the bloodstream.

By an "effective" amount of a drug or pharmacologically active agent is meant a nontoxic but sufficient amount of the drug or agent to provide the desired effect. The exact amount required will vary from subject to subject, depending on the species, age, and general condition of the subject, the severity of the condition being treated, the drug or agent being employed, the mode of administration, and the like. Thus, it is not possible to specify an exact "effective amount." However, an appropriate "effective" amount in any individual case may be determined by one of ordinary skill in the art using routine experimentation.

Figures 1, 2:
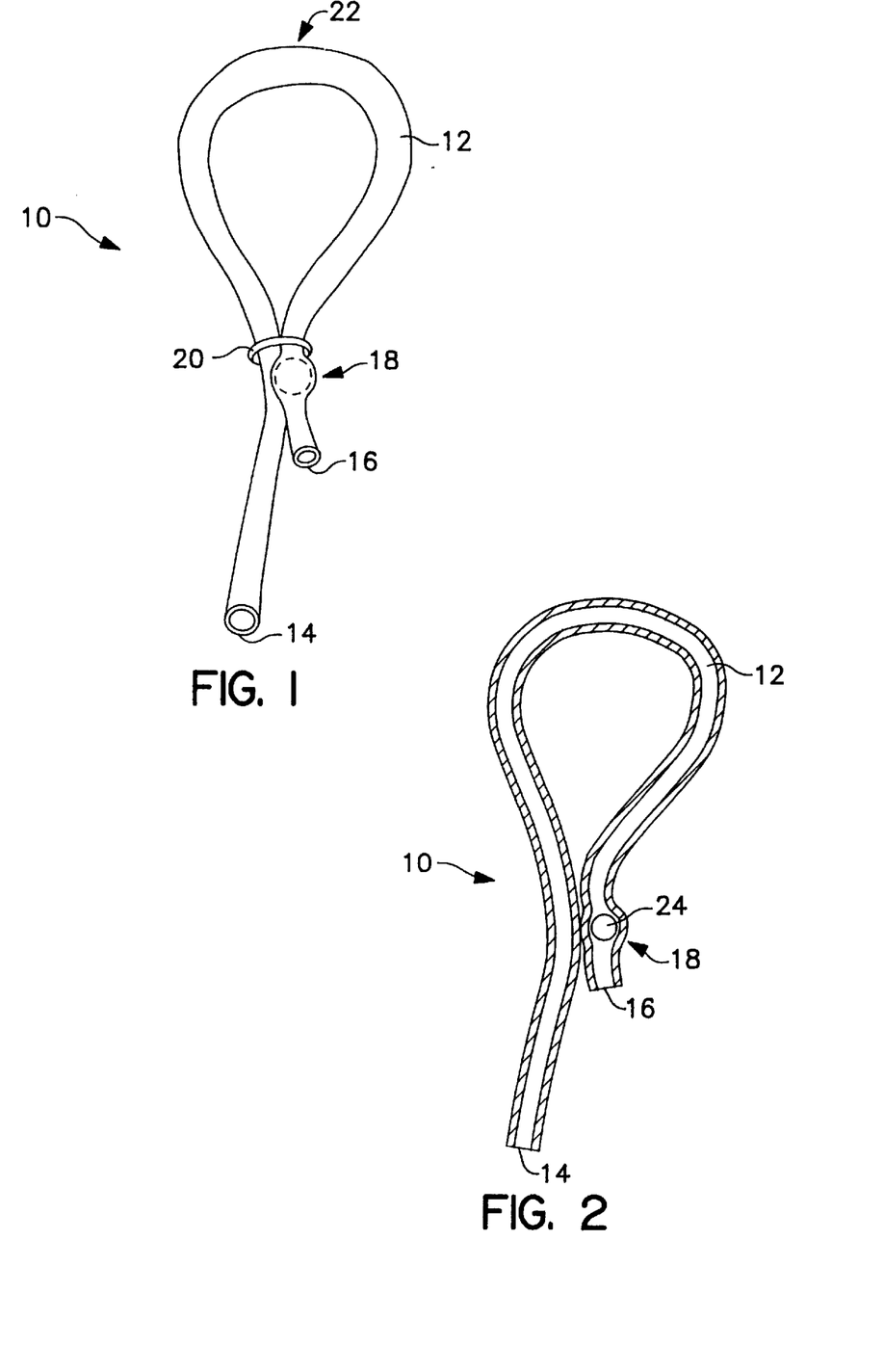
FIG. 1 is a perspective view of a venous flow control device in a loop configuration.
FIG. 2 is a cross-sectional view of the device of FIG. 1 showing an integral fastening means disposed within the tubing of the device.

In one embodiment, the invention relates to a venous flow control device ("VFC") adapted for application to the penis. The device can be used to maintain a penile erection, enhance a penile erection, or help in the treatment of incontinence. Referring to FIG. 1, one embodiment of a VFC device is generally indicated at 10. The device 10 is formed from a length of tubing having a central section 12 flanked by a distal end 14 and a proximal end 16. The central section of the tubing has a substantially uniform diameter. The length of the tubing may be selected to custom fit any individual user in either a pre-scrotal or post-scrotal position.

The device 10 further includes an integral fastening means adapted to hold and secure the tubing in the form of a loop having an adjustable size. The integral fastening means is provided in part by a substantially rigid, enlarged segment of tubing 18 substantially adjacent to the proximal end 16 of the tubing. The enlarged segment of tubing operates in combination with an associated annular ring 20 to provide a ball and ring coupling configuration. Specifically, a loop, indicated at 22, is formed by folding a portion of the central section 12 of the tubing on itself and threading the folded section through the ring 20. The central opening of the ring is dimensioned such that the tubing may be maintained in a loop formation; however, the overall size of the loop 22 is readily adjustable by pulling a desired length of the tubing through the ring. Once the loop has been adjusted to a particular size, the device is locked by sliding the ring 20 into close engagement with the enlarged segment 18 of the tubing. As can be seen by reference to FIG. 1, the enlarged segment of tubing has a larger diameter than that of the central section 12 of the tubing. This feature prevents the passage of the enlarged section through the annular ring and allows the device 10 to be maintained in the form of loops having various selected sizes. The device 10 is thus quite simple in structure and can be formed from readily available materials such as surgical tubing and O-ring gaskets. This provides ease and economy of manufacture, particularly when compared to prior composite constriction devices which employ unique and/or specialized components.

The tubing 12 may be manufactured from any number of materials, and the selection of a particular material will depend on criteria such as user sensitivities, therapeutic device regulatory guidelines and/or a number of material characteristics. Preferably, the VFC device is formed from a highly stretchable, flexible elastomer which has sufficient tensile strength to withstand a substantial degree of stretch and maintains its elasticity over time and repeated use.

Particularly preferred materials for tubing 12 include natural gum rubber, surgical rubber or latex rubber, as well as synthetic elastomers such as silicones and copolymers well known in the art. Latex rubber exhibits particularly preferred elastomeric characteristics, but may cause sensitization in a small percentage of the population. These materials can also include one or more colorants present at about 0.5 to 10 wt. %. An example of a preferred latex material is an off-white colored latex containing about 6 wt. % $TiO_2$.

Silicone tubing structures are also well known in the art. Silicone tubing is generally capable of full recovery after deformation, and can be sealed or bonded to render structures air-tight, i.e., using silicone that has been liquified by heating. Other materials which are useful herein include, but are not limited to, natural and synthetic elastomers such as butyl rubber, polyurethane rubber, polysiloxane elastomers such as methyl vinyl polysiloxane or the like, block copolymers such as Kraton® (Shell Oil Company, Houston, Tex.) or the like, ethylene/propylene copolymers, polyisobutylene, chloroprene polymers, polybutadiene, polyisoprene and natural rubbers. Additional materials will be readily apparent to those of skill in the art. Tubing structures formed from such materials may be fabricated using conventional techniques, e.g., compression, transfer or injection molding procedures.

Ring 20 can comprise any material which is sufficiently rigid to hold its shape. The ring should have a smooth surface to facilitate device assembly and adjustment of loop size. In addition, the ring material preferably has a coefficient of static friction with respect to the tubing material which allows the tubing to easily slide within and against the ring when the size of the loop is being adjusted. Particularly preferred ring materials include polycarbonates (such as Lexan®) or polystyrenes. Another preferred ring material is polytetrafluoroethylene, such as wherein the annular ring 20 comprises a Teflon® O-ring. It has been found herein that Lexan® exhibits particularly superior frictional characteristics when used in combination with latex tubing materials.

Referring now to FIGS. 1 and 2, the enlarged segment 18 of tubing is provided by a substantially spherical body 24 within the tubing at the proximal end 16 thereof. The spherical body has a diameter greater than that of the diameter of the remainder of the tubing. When the body is inserted into the tubing, then, the tubing stretches about the body to provide a substantially rigid, enlarged tubing segment. Body 24 is held in place adjacent to the proximal end 16 of the tubing and, because of the grip provided by the stretched tubing material, resists any lateral movement within the tubing. The body 24 is generally formed from a metallic material, a substantially nondeformable polymeric material, or other rigid materials. For example, body 24 may comprise a polyethylene or polypropylene ball. Here again, the fact that commonly available materials such as polyethylene or polypropylene may be used reduces the cost and difficulty of manufacturing the present devices.

Figure 3:
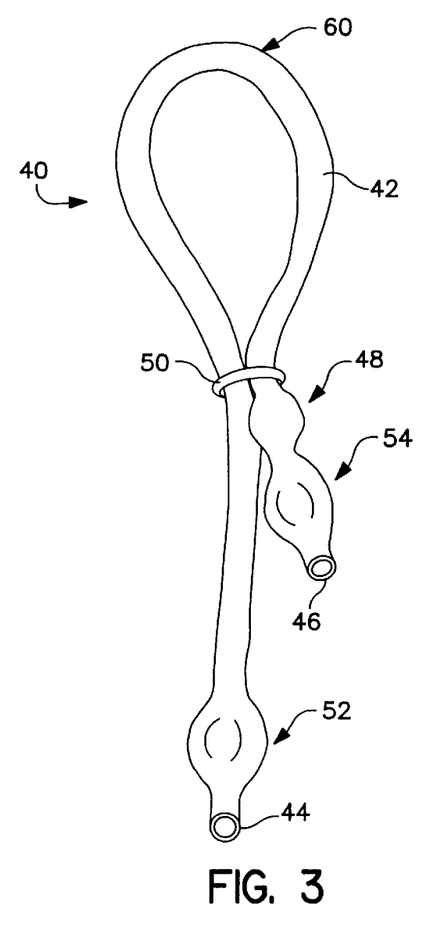
FIG. 3 is a perspective view of an alternative venous flow control device in a loop configuration.

In a related embodiment of the invention, a VFC device is provided with grasping means which facilitate the manipulation and adjustment of the device. Referring to FIG. 3, one such VFC device is shown generally at 40. The device 40 is formed from tubing having a central section 42 flanked by a distal end 44 and a proximal end 46. The device 40 also includes an adjustable integral fastening means that can maintain the tubing in the form of a loop of adjustable size, wherein the integral fastening means comprises the operative combination of a substantially rigid, enlarged segment of tubing 48 adjacent to the proximal end 46 of the tubing and an associated ring 50. The device has been assembled as previously described to provide a loop, generally indicated at 60. A first grasping means 52 is present adjacent to the distal end 44 of the tubing. A second grasping means 54 is present between the proximal end 46 of the tubing and the enlarged segment 48 of the tubing. The first and second grasping means generally comprise areas of tubing having increased diameter with resect to the diameter of the remainder of the tubing. These areas provide finger grasps that allow an individual to manipulate the device more easily, such as when adjusting the device in place about the individual's penis.

Figure 4:
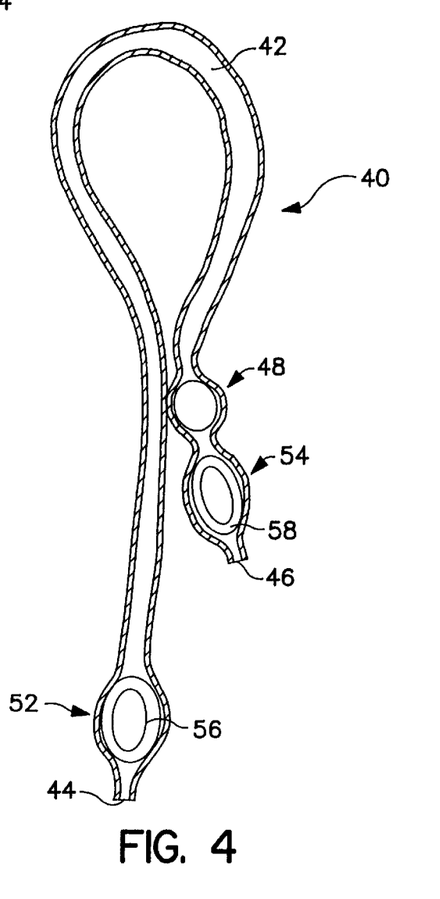
FIG. 4 is a cross-sectional view of the device of FIG. 3 showing optional finger grasping means disposed within the tubing of the device.

The grasping means 52 and 54 can be formed by compressing the tubing at its distal and proximal ends 44 and 46 to provide substantially flattened areas of increased diameter. When the tubing comprises an elastomeric or flexible material, the flattened areas can be formed using heat sealing techniques, or a bonding agent such as a suitable adhesive. However, the grasping means are preferably provided by bodies that are contained within the tubing. Referring now to FIGS. 3 and 4, the first 52 and second 54 grasping means are formed from annular bodies 56 and 58, respectively, which are contained within the tubing at the distal and proximal ends thereof. The annular bodies 56 and 58 have diameters sufficient to cause the tubing to stretch into flattened discs of increased diameter relative to the diameter of the central section 42 of the tubing. The annular bodies also serve to close and substantially seal the VFC device at both ends. In this manner, one possible source of contamination is avoided by closing off the interior of the tubing. The device 40 can thus be effectively re-used in a sanitary fashion by cleaning the surface using soap and water.

Figure 5:
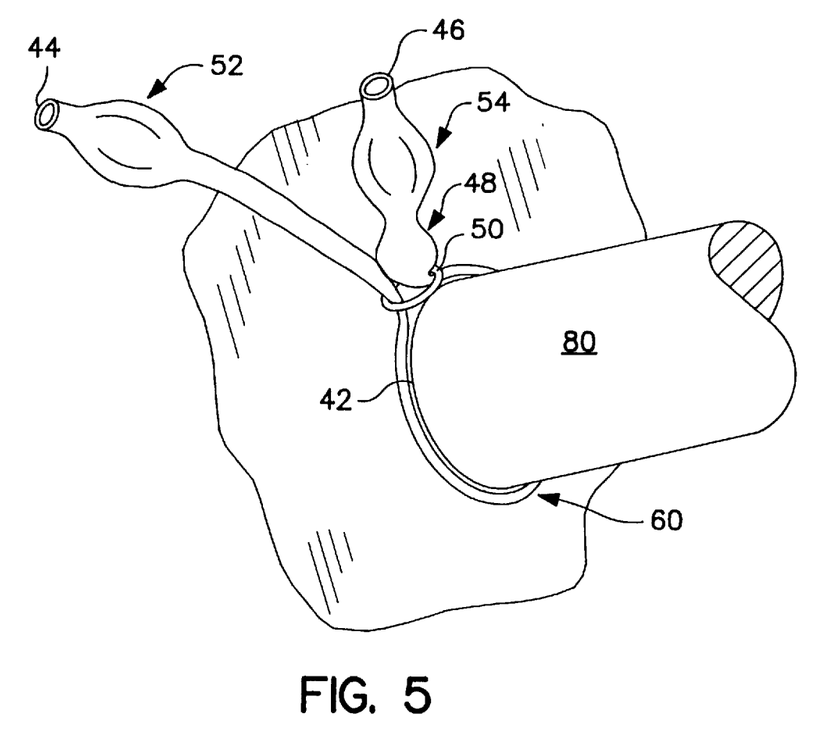
FIG. 5 is a pictorial representation of a venous flow control device in use.

Referring now to FIG. 5, the device 40 is shown in place about the base of an individual's penis 80 in a post-scrotal position. The device is first brought into a loop configuration by passing a portion of the tubing through the ring 50. An initial setting is established by drawing a sufficient length of tubing through the ring to provide a loop 60 of maximum size. The size of the loop is maintained by locking the device with the ball and ring coupler. The device can then be applied by grasping the loop 60 and stretching the tubing to increase the size of the loop. The penis is inserted through the stretched loop and the VFC device slid over the shaft of the penis until it is positioned around the base thereof. As depicted in FIG. 5, the VFC device 40 is preferably positioned with the distal and proximal ends, 44 and 46, of the tubing arranged to one side of the shaft of the penis with the enlarged portion of tubing 48 protruding through the annular ring 50 above the remaining section of tubing that passes through the ring. Device 40 is adjusted by grasping the distal end 44 of the tubing at the first finger grip 52 and pulling the tubing until the loop 60 is tightened as desired about the base of the penis or around both the base of the penis and the scrotum.

In use, the VFC device is tightened to provide increased circumferential tension about the penis. In particular, the distal end 44 is grasped and pulled downwardly to draw the tubing through the ring, thereby decreasing the size of the loop 60. The device is maintained at its tensioned setting by the resilient engagement of the enlarged segment 48 of tubing with both the ring 50 and a portion of the central section 42 that passes through the ring. Thus, the device 40 provides an even, radial compressive force on the penis sufficient to limit the outflow of blood from the penis during the erectile process without substantially obstructing arterial inflow.

As the penis becomes erect, the VFC device may be further tightened or loosened as necessary to achieve and/or maintain erection and comfort. The ball and ring coupling provided by the integral fastening means serves to maintain the selected tension setting by resisting movement in response to outward pressure exerted by the penis during the erectile process. However, as the penis develops increased turgidity, the extent of outward pressure may reach a threshold where the VFC device needs to be re-adjusted to a decreased tension setting by providing a slightly greater loop size. This loosening operation involves grasping the proximal end 46 of the tubing at the second finger grip 54 and pulling the tubing upward to partially disengage the enlarged segment 48 of the tubing from its coupling seat in the annular ring 50. In this manner, the size of the loop 60 can be incrementally increased to provide delicate control over the tension provided by the device.

The ability to control and adjust the degree of tension provided by the VFC device allows the individual to avoid excessive venous flow occlusion which can prevent deep tissue transfer throughout the cavernosa, resulting in occurrence of a partial erection, e.g., an erection occurring distal to the device. Excessive occlusion can lead to a hinged erection such as those failed erections that have been encountered with prior pump and occlusive band devices. By contrast, the adjustable pressure exerted by the VFC device allows only the superficial venous and spongiosal systems to be affected, allowing the entire length of the cavernosa to fill to yield a normal erection.

Accordingly, these and further related embodiments of the invention provide a safe and effective means to assist an individual in the maintenance of a penile erection. The devices simulate the normal erectile process by providing vaso-constriction such as that normally effected by sphincter muscles at the base of the penis to interrupt the veinal blood flow therefrom during erection, thereby causing an imbalance in blood flow rates to and from the penis. When properly adjusted, the devices supply a radial compressive force effective to impede blood flow from the penis via the peripheral veins, while blood flow to the penis via the deeply embedded arteries remains substantially unimpeded. Thus, the devices interrupt venous leakage and are useful in the maintenance of an erection.

In another embodiment of the invention, a method is provided for maintaining penile erection in a male individual using the VFC device. In order to carry out the method, the VFC device is provided which has a tubing length sufficient to fit around the base of an individual's penis, in either a pre-scrotal or post-scrotal position. When used in the pre-scrotal position, the tubing encircles the base of the penis and passes behind the scrotum at the junction of the pubis. Some individuals may find that such pre-scrotal positioning is more comfortable or more effective than post-scrotal application. In both positions, the device is used to encircle the base of the penis and is brought into a tensioned setting by drawing on one end of the tubing such that the size of the loop is decreased. As explained above, this helps restrict veinal out-flow from the penis. The device may optionally be applied to the individual's penis after enlargement to help maintain an erection, such as when the user does not require assistance in achieving an erection. The device can also be used to enhance penile erection, or to enhance penile size attained with erection.

The invention also extends to a method for treating erectile dysfunction in a male individual wherein application of the device is coupled with therapeutic administration of a selected vasoactive or androgenic agent within the context of a dosing regimen effective to assist in the treatment of erectile dysfunction. Suitable dosage regimens will be known to those skilled in the art or may be readily determined. The amount of active agent administered will, of course, be dependent on the subject being treated, the mode of administration, and the judgment of the prescribing physician.

Suitable vasoactive agents include, but are not limited to: nitrates such as nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine ("SNAP"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogues, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone; naturally occurring prostaglandins such as $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptide.

Prazosin, prostaglandin $E_1$ and prostaglandin $E_2$ are particularly preferred vasoactive agents for use in conjunction with the present method. Additionally, simultaneous administration of two or more vasoactive agents may be desirable and in some cases exhibit a synergistic effect. The combinations are administered within the context of an effective dosing regimen to take advantage of the combined effect. Preferred combinations of vasoactive agents include, for example, combinations of an α-blocker with a prostaglandin such as the combination of prazosin with prostaglandin $E_1$.

Suitable androgenic agents include, but are not limited to: the naturally occurring androgens androsterone, testosterone and dehydroepiandrosterone (DHEA); pharmaceutically acceptable esters of testosterone; and pharmaceutically acceptable derivatives of testosterone. Testosterone esters are generally formed from the hydroxyl group present at the C-17 position, and particularly preferred esters are the enanthate, propionate, cypionate and phenylacetate esters of testosterone. Exemplary pharmaceutically acceptable derivatives of testosterone include, but are not limited to, methyltestosterone, testolactone, oxymetholone and fluoxymesterone. Accordingly, in one aspect of the invention, the present VFC devices are used in combination with the administration of an androgenic agent such as is described in commonly assigned U.S. patent application Ser. No. 08/662, 677, entitled "Transurethral Administration of Androgenic Agents to Prevent and/or Treat Erectile Dysfunction."

Transurethral administration of the agent is preferred although not essential. Use of the VFC device in conjunction with transurethral administration of the agent allows for the enhanced retention of the administered agent within the penis. The agent will typically be administered in a pharmaceutical composition comprising an effective amount of the agent, a vehicle suitable for transurethral drug delivery, and, optionally, a transurethral permeation enhancer. The vehicle is selected from any of a number of common materials known in the art, e.g., any liquid, gel, solvent, liquid diluent, solubilizer, or the like, which is nontoxic and which does not interact with other components of the composition in a deleterious manner. Other types of components may be incorporated into the pharmaceutical composition as well, for example, surfactants, preservatives (e.g., antioxidants), stabilizers, enzyme inhibitors, and the like, as will be appreciated by those skilled in the art of drug formulation preparation and delivery.

As explained in PCT Publication No. WO91/16021, transurethral administration of a pharmaceutical agent can be carried out in a number of different ways. For example, the agent can be introduced into the urethra from a flexible tube, squeeze bottle, pump or aerosol spray. The agent may also be contained in coatings, pellets or suppositories which are absorbed, melted or bioeroded in the urethra. In certain embodiments, the selected agent may be included in a coating on the exterior surface of a penile insert.

Various transurethral drug delivery devices are known in the art, and can be used in the practice of the methods herein. Such devices generally deliver the agent at least about 3 cm into the urethra, and preferably at least about 7 cm in to the urethra. Examples of devices suited to deliver a drug transurethrally include those described and illustrated in WO91/ 16021. The devices can either be manufactured under sterile conditions, thereby eliminating the need for post-manufacturing sterilization, or they can be manufactured under non-sterile conditions and then subsequently sterilized by any suitable technique, e.g., radiation sterilization.

Transurethral compositions may further include one or more permeation enhancers which increase the permeability of the urethral wall to agents administered as described herein and thereby increase the rate at which those agents enter the bloodstream. Transurethral permeation enhancers useful herein include, but are not limited to, dimethylsulfoxide (DMSO), dimethyl formamide (DMF), N,N-dimethylacetamide (DMA), decylmethylsulfoxide ($C_{10}MSO$), polyethylene glycol monolaurate (PEGML), propylene glycol, glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), alcohols, or the like.

Further, to facilitate insertion of the transurethral agent, a pharmaceutical composition may include a coating having lubricating properties. Such coatings may contain materials such as polyethylene glycol ("PEG"), propylene glycol, or hydroxy alkyl celluloses, for example, which are or become slippery upon insertion into the urethra. Materials such as glycerol monolaurate, polyethylene glycol monolaurate, and glycerol monolaurate, for example, may combine permeation enhancing properties with lubricating properties.

The pharmaceutical composition may additionally include one or more enzyme inhibitors designed to inhibit any agent-degrading enzymes which may be present in the urethra. Such enzyme inhibiting compounds may be determined by those skilled in the art by reference to the pertinent literature and/or using routine experimental methods.

In other aspects of the invention, the vasoactive or androgenic agent may be administered topically, transdermally or by any other available and effective means such as by intracavernosal injection. However, transurethral administration is highly preferred as it is generally far more effective with many types of agents. Nevertheless, it may sometimes be desirable to deliver the agent using an alternative mode of administration.

In connection with therapeutic administration of vasoactive or androgenic agents, the VFC devices of the present invention provide a particularly useful adjunct in the treatment of erectile dysfunction wherein those devices serve to prevent the flow of blood from the penis, thereby increasing the transient retention of an administered agent within the penis. As will be appreciated by those skilled in the art, increased retention of such agents within the penis serves to improve the effectiveness of drug administration. Concurrent use of the VFC device as described herein results in from at least a two-fold to a ten-fold or greater increase in the dose response efficacy of an administered vasoactive agent in the treatment of erectile dysfunction. Thus, these devices may be used to render effective an otherwise ineffective dose of a vasoactive agent, such as when a user has experienced incomplete response to drug administration due to excessive venous leakage. Furthermore, use of the present devices in connection with drug administration allows lower dosages of vasoactive or androgenic agents to be used.

It is thought that the terminal shaft and glans of the human penis have extensive vascular interconnections with the interior of the corpus cavernosa. The extent of such vascularization, although variable, is sufficient to cause drug transfer problems in topical and transdermal drug administration. Adsorption of topically applied agents through the skin of the penis is generally not sufficiently rapid to overcome the concomitant superficial venous drainage, the drainage of the glans, and distal non cavernosal transfer into the spongiosa, each of which serve to clear the agent from the penis. Thus, prior attempts at topical or transdermal application of agents to the skin of the penis in the treatment of erectile dysfunction have not provided consistent satisfactory erections in light of the minimal cavernosal transfer caused by exodus of the agents from the cavernosum.

However, use of a VFC device as described hereinabove in conjunction with topical, transdermal or intracaverosal administration of therapeutic agents enables enhanced drug retention in the corpora cavernosa and results in enhanced effectiveness of drug therapy. The VFC device applies a mild, adjustable pressure about the periphery of the penis which is sufficient to occlude the superficial venous and spongiosa drainage. Drug transfer problems are thus avoided, and the administered agent is retained within the penis, allowing movement into the corpus cavernosa. This produces smooth muscle response and a consistent erectile response.

The ability to control and adjust the tension provided by the novel VFC device also allows for use in methods to prevent urinary incontinence. Accordingly, in a further embodiment of the invention, a method is provided for preventing involuntary passage of urine from the urethra in an incontinent male individual. The method involves encircling the base of the penis with a VFC device as provided herein. The device can be tensioned about the penis to occlude the urethra and prevent involuntary passage of urine therethrough. The device can be readily loosened when the individual wishes to void, and then re-tensioned. In a related embodiment, the VFC device can be structured so as to exert additional pressure on the urethra.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

EXAMPLE 1

Use of Venous Flow Control Device to Provide Improved Erectile Response to Transurethral Drug Administration Transurethral and intracavernosal administration of alprostadil (prostaglandin $E_1$) have been shown to be effective in the treatment of erectile dysfunction. However, some patients are still unable to achieve adequate veno-occlusion using such local pharmacotherapy. Accordingly, the venous flow control (VFC) device 40 depicted in FIGS. 3 and 4 was used in conjunction with transurethral alprostadil administration in patients previously unresponsive to transurethral therapy alone, to assess the ability of the device to supplement or improve the efficacy of such pharmacotherapy in the treatment of impotence.

The experimental group included eight individuals who had been nonresponsive to transurethral alprostadil therapy in the treatment of erectile dysfunction. Each individual underwent color-flow duplex ultrasound evaluation following a 500 $\mu$g dose of alprostadil administered transurethraly. Drug was administered to each individual twice: on one day without the VFC device; and, on a separate day, with the VFC device. The order of administration of alprostadil with and without the device was randomized throughout the experimental group. When the VFC device was used, the loop was positioned about the base of the penis and tensioned firmly prior to transurethral alprostadil administration. Tension provided by the device was adjusted for comfort 10 minutes after drug administration. Peak systolic velocity (PSV) and end diastolic velocity (EDV) were measured after drug administration, and the values obtained were used to calculate the erectile resistivity index (RI). Subjective patient observations of penile rigidity were also recorded and scored on a scale of 1–5, wherein 1=no response, and 5=rigid.

Evaluation of the results of the investigation showed that use of the VFC device with transurethral alprostadil administration increased the mean (±SE) reported penile rigidity to 3.6±0.4, from a mean of 2.4±0.3 obtained without use of the device (p=0.02). Six out of the eight individuals in the experimental group who had previously failed transurethral alprostadil therapy were able to achieve an erection sufficient for intercourse by using the VFC device in connection with the pharmacotherapy. The mean duration of erection sufficient for intercourse also increased significantly, from 1.3±1.3 minutes without the device, to 14±3.6 minutes with the device (p=0.01). Hemodynamic measurements using duplex ultrasound showed an increase in RI (0.67 to 0.78, p=0.07), as well as a trend toward a decrease in end diastolic velocity (EDV), when the VFC device was used. No significant difference in peak systolic velocity was observed between measurements obtained after transurethral alprostadil administration alone, or transurethral alprostadil administration in conjunction with use of the VFC device.

Accordingly, the results indicate that use of the VFC device in combination with transurethral alprostadil administration can improve both penile rigidity and the duration of an erection that is sufficient for intercourse.

I claim:

1. A device for application to a human penis and adapted to maintain a penile erection, comprising:
    a length of flexible tubing to be applied to the penis as a loop, having distal end, a proximal end, and a central section having a substantially uniform diameter, wherein the tubing is provided with first and second grasping means adjacent to the distal and proximal ends of the tubing, respectively; and
    a tension-relieving means for adjusting constrictive tension after application of the device to the penis,
    wherein the tension-relieving means comprises an integral fastening means adapted to secure the tubing in the form of a loop of adjustable size, in turn comprising (i) a substantially rigid, enlarged segment of tubing between said first and second grasping means substantially adjacent to the proximal end of the tubing and (ii) a ring through which a loop of the central section of tubing may be passed, wherein the ring is dimensioned to maintain the tubing in the form of a loop while also allowing adjustment of the size of the loop, and further wherein the enlarged segment of tubing has a diameter which prevents its passage through the ring.

2. The device of claim 1, wherein the substantially rigid, enlarged segment of tubing is provided by a substantially spherical body contained within the tubing.

3. The device of claim 2, wherein the substantially spherical body is comprised of a polymeric material.

4. The device of claim 3, wherein the polymeric material is polyethylene or polypropylene.

5. The device of claim 1, wherein the tubing is comprised of a latex material.

6. The device of claim 5, wherein the latex material comprises about 0.5 to 10 wt. % pigment.

7. The device of claim 6, wherein the pigment is titanium dioxide.

8. The device of claim 1, wherein the ring is comprised of a polycarbonate.

9. The device of claim 1, wherein the length of the tubing is such that the loop fits around both a penis and the scrotum at the junction of the pubis.

10. A method of maintaining penile erection in a male individual, comprising:
    (a) providing a device comprised of a length of flexible tubing to be applied to the penis as a loop, having a distal end, a proximal end, and a central section having a substantially uniform diameter, wherein the tubing is provided with first and second grasping means adjacent to the distal and proximal ends of the tubing, respectively, and wherein the device further includes a tension-relieving means for adjusting constrictive tension after application of the device to the penis, said tension-relieving means comprising an integral fastening means adapted to secure the tubing in the form of a loop of adjustable size, in turn comprising (i) a substantially rigid, enlarged segment of tubing between said first and second grasping means substantially adjacent to the proximal end of the tubing and (ii) a ring through which a loop of the central section of tubing may be passed, wherein the ring is dimensioned to maintain the tubing in the form of a loop while also allowing adjustment of the size of the loop, and further wherein the enlarged segment of tubing has a diameter which prevents its passage through the ring; and
    (b) encircling the base of the individual's penis with said loop and tensioning the device thereabout to provide circumferential tension sufficient to prevent excess venous outflow from the penis, wherein tensioning comprises pulling on the distal end of the tubing to reduce the size of the loop and bring the enlarged segment of tubing into close locking engagement with both the ring and a central section of the tubing.

11. The method of claim 10, further including the step of reducing the circumferential tension provided by the tensioned device during erection so as to retain blood within the penis without substantially obstructing arterial inflow.

12. The method of claim 11, wherein reducing the tension is carried out by pulling on the proximal end of the tubing to disengage the enlarged segment of tubing from its close locking engagement with the ring and the central section of the tubing, thereby allowing the size of the loop to be increased.

13. The method of claim 12, wherein step (b) comprises encircling both the penis and scrotum at the junction of the pubis.

14. The method of claim 13, further including the step of reducing the circumferential tension provided by the tensioned device during erection so as to retain blood within the penis without substantially obstructing arterial inflow.

15. The method of claim 14, wherein reducing the tension is carried out by pulling on the proximal end of the tubing to disengage the enlarged segment of tubing from its close locking engagement with the ring and the portion of the central section of the tubing, thereby allowing the size of the loop to be increased.

16. A method for treating erectile dysfunction in a male individual, comprising:
    (a) administering a pharmacologically active agent to the individual;
    (b) providing a device comprised of a length of flexible tubing to be applied to the penis as a loop, having a distal end, a proximal end, and a central section having a substantially uniform diameter, wherein the tubing is provided with first and second grasping means adjacent to the distal and proximal ends of the tubing, respectively, and wherein the device further includes a tension-relieving means for adjusting constrictive tension after application of the device to the penis, said tension-relieving means comprising an integral fastening means adapted to secure the tubing in the form of a loop of adjustable size, in turn comprising (i) a substantially rigid, enlarged segment of tubing between said first and second grasping means substantially adjacent to the proximal end of the tubing and (ii) a ring through which a loop of the central section of tubing may be passed, wherein the ring is dimensioned to maintain the tubing in the form of a loop while also allowing adjustment of the size of the loop, and further wherein the enlarged segment of tubing has a diameter which prevents its passage through the ring; and (c) encircling the base of the individual's penis with said loop and tensioning the device thereabout to provide circumferential tension sufficient to prevent excess venous outflow from the penis and cause enhanced retention of the agent within the penis, wherein said tensioning comprises pulling on the distal end of the tubing to reduce the size of the loop and bring the enlarged segment of tubing into close locking engagement with both the ring and a portion of the central section of the tubing.

17. The method of claim 16, wherein step (c) comprises encircling both the penis and scrotum at the junction of the pubis.

18. The method of claim 17, wherein the agent is administered transurethrally.

19. The method of claim 18, wherein the agent is an androgenic agent.

20. The method of claim 19, wherein the androgenic agent is selected from the group consisting of androsterone, testosterone, dehydroepiandrosterone, testosterone enanthate, testosterone propionate, testosterone cypionate, testosterone phenylacetate, methyltestosterone, testolactone, oxymetholone, fluoxymesterone, and combinations thereof.

21. The method of claim 18, wherein the agent is a vasoactive agent.

22. The method of claim 21, wherein the vasoactive agent is an α-blocker selected from the group consisting of phenoxybenzamine, dibenamine, doxazosin, terazosin, phentolamine, tolazoline, prazosin, trimazosin, alfuzosin, tamsulosin and indoramin.

23. The method of claim 21, wherein the vasoactive agent is selected from the group consisting of prazosin, prostaglandin $E_1$, prostaglandin $E_2$, and combinations thereof.

24. The method of claim 21, wherein the vasoactive agent is a nitrate selected from the group consisting of nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine.

25. The method of claim 16, wherein the agent is administered transurethrally.

26. The method of claim 25, wherein the agent is an androgenic agent.

27. The method of claim 26, wherein the androgenic agent is selected from the group consisting of androsterone, testosterone, dehydroepiandrosterone, testosterone enanthate, testosterone propionate, testosterone cypionate, testosterone phenylacetate, methyltestosterone, testolactone, oxymetholone, fluoxymesterone, and combinations thereof.

28. The method of claim 25, wherein the agent is a vasoactive agent.

29. The method of claim 28, wherein the vasoactive agent is an α-blocker selected from the group consisting of phenoxybenzamine, dibenamine, doxazosin, terazosin, phentolamine, tolazoline, prazosin, trimazosin, alfuzosin, tamsulosin and indoramin.

30. The method of claim 28, wherein the vasoactive agent is selected from the group consisting of prazosin, prostaglandin $E_1$, prostaglandin $E_2$, and combinations thereof.

31. The method of claim 28, wherein the vasoactive agent is a nitrate selected from the group consisting of nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine.

32. A method for preventing urinary incontinence in a male individual, comprising: (a) providing a device comprised of a length of flexible tubing to be applied to the penis as a loop, having a distal end, a proximal end, and a central section having a substantially uniform diameter, wherein the tubing is provided with first and second grasping means adjacent to the distal and proximal ends of the tubing, respectively, and wherein the device further includes a tension-relieving means for adjusting constrictive tension after application of the device to the penis, said tension-relieving means comprising an integral fastening means adapted to secure the tubing in the form of a loop of adjustable size, in turn comprising (i) a substantially rigid, enlarged segment of the tubing between said first and second grasping means substantially adjacent to the proximal end of the tubing and (ii) a ring through which a loop of the central section of tubing may be passed, wherein the ring is dimensioned to maintain the tubing in the form of a loop while also allowing adjustment of the size of the loop, and further wherein the enlarged segment of tubing has a diameter which prevents its passage through the ring; and (b) encircling the base of the individual's penis with said loop and tensioning the device thereabout to provide circumferential tension sufficient to prevent involuntary passage of urine from the individual's urethra, wherein tensioning comprises pulling on the distal end of the tubing to reduce the size of the loop and bring the enlarged segment of tubing into close locking engagement with both the ring and a portion of the central section of the tubing.

* * * * *